US00PP14973P2

(12) United States Plant Patent
Austin

(10) Patent No.: US PP14,973 P2
(45) Date of Patent: Jun. 29, 2004

(54) SHRUB ROSE PLANT NAMED 'AUSBITE'

(50) Latin Name: *Rosa hybrida*
Varietal Denomination: AUSbite

(75) Inventor: David C. H. Austin, Albrighton (GB)

(73) Assignee: David Austin Roses Limited, Albrighton (GB)

( * ) Notice: Subject to any disclaimer, the term of this patent is extended or adjusted under 35 U.S.C. 154(b) by 0 days.

(21) Appl. No.: 10/615,897

(22) Filed: Jul. 8, 2003

(51) Int. Cl.[7] ..... A01H 5/00
(52) U.S. Cl. ..... Plt./107
(58) Field of Search ..... Plt./107, 108

*Primary Examiner*—Bruce R. Campell
*Assistant Examiner*—Annette H Para

(57) ABSTRACT

Shrub/climber rose plant having soft pink, cupped flowers filled with numerous petals; vigorous, bushy growth and a good fragrance with a hint of myrrh.

1 Drawing Sheet

Genus and Species: *Rosa hybrida*
Variety Denomination: 'AUSbite'

ORIGIN OF THE INVENTION

The present invention relates to a new and distinct variety of a shrub rose plant named 'AUSbite' which was originated by me by crossing the variety 'AUScot', U.S. Plant Pat. No. 7,215, with an unnamed seedling.

BACKGROUND OF THE INVENTION

The primary objective of this breeding was to produce a new rose variety having soft pink flowers, good fragrance, and high disease resistance.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Soft pink, cupped flowers with numerous petals.
2. Vigorous, bushy growth.
3. Good fragrance with a hint of myrrh.

Asexual reproduction of this new variety by budding, as performed at Albrighton, England, shows that the foregoing and all other characteristics and distinctions come true to form and are established and transmitted through succeeding propagations.

Comparison with Parents

'AUScot' (Abraham Darby), is a well rounded shrub bearing large apricot cup-shaped flowers. The female parent has large globular flowers of a deeper pink than AUSbite.

Comparison with Similar Variety

'AUStop' (U.S. Plant Pat. No. 11,423) has blush pink blooms on a shrubby, twiggy plant, whereas 'AUSbite' has soft pink blooms and forms a substantial bushy shrub.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of a new rose cultivar with color descriptions using terminology in accordance with The Royal Horticultural Society (London) Colour Chart (2001), except where ordinary dictionary significance of color is indicated.

Parentage:
*Seed parent.*—Unnamed Seeding. (Unpatented).
*Pollen parent.*—'AUScot' (U.S. Plant Pat. No. 7,215).

FLOWER

Observations made from plants commencing at one year of age grown in a garden environment at Albrighton, England.

Blooming Habit: Recurrent.
Bud:
*Size.*—About 2.6 cm long and 2 cm in diameter when the petals start to unfurl.
*Form.*—The bud form is globular.
*Color.*—When sepals first divide, bud color is Yellow-Green Group 144A. When half blown, the upper sides of the petals are Purple Group 75B; and the lower sides of the petals are Purple Group 75D.
*Sepals.*—Color: Upper surface: Yellow-Green Group 144A. Lower surface: Yellow-Green Group 144A. Length: 2.9 cm. Width: 1.3 cm. Shape: Pointed. Surface texture: Hairy edges. Upper surface: Slightly hairy. Lower surface: Smooth. There are three normally appendaged sepals. There are two unappendaged sepals with hairy edges.
*Receptacle.*—Color: Yellow-Green Group 144A. Shape: Pitcher. Size: Medium, about 1.5 cm long×1.2 cm wide. Surface: Smooth.

*Peduncle.*—Length: Medium, averaging about 5 cm. Surface: Prickly. Color: Yellow-Green Group 144B. Strength: Erect.

Bloom:

*Size.*—Large. Average open diameter is about 7.1 cm.

*Borne.*—Several together in flat clusters of fifteen blooms, the clusters being of irregular shape.

*Stems.*—Strength: Strong. Average length is about 50 cm with a diameter of 0.6 cm.

*Form.*—When first open: Cupped. Permanence: Outer petals curl back.

*Petalage.*—Number of petals under normal conditions: 200.

*Color.*—The upper sides of the petals are Purple Group 75D at their outermost portion, Purple Group 75C in the middle and Purple Group 75B towards the base. The reverse sides of the petals are Purple Group 75D at the outermost portion and Purple Group 75B towards the base. The base of each petal has a Yellow Group 9B spot. The major color on the upper side is Purple Group 75B.

*Variegations.*—None.

*Discoloration.*—The general tonality at the end of the first day: No change. At the end of the third day: Fading to Purple Group 75C.

*Fragrance.*—Moderate with a hint of myrrh.

Petals:

*Texture.*—Thick.

*Size.*—Width: 3.7 cm. Length: 3.8 cm.

*Surface.*—Smooth, both upper and lower.

*Shape.*—Round; notched. Margin: Weak reflexing. Apex Shape: Rounded. Base Shape: Pointed.

*Form.*—Tips slightly recurved.

*Arrangement.*—Informal.

*Petaloids.*—Tucked in calyx.

*Persistence.*—Petals hang on and dry.

*Lastingness.*—On the plant: Fair (about 4 days). As a cut flower: Short (about 3 days).

Reproductive parts:

*Stamens.*—Number: 96. Length: 0.2 cm. Arrangement: Tucked in calyx. Anthers: Length: 0.2 cm. Color: Yellow-Orange Group 14A. Filaments: Color: Yellow-Green Group 145C. Length: 0.4 cm. Pollen: Color: Yellow-Orange Group 17B.

*Pistils.*—Number: 15. Styles: Color: Yellow-Green Group 145A. Length: 0.6 cm. Stigmas: Color: Yellow-Green Group 150C. Length: 0.1 cm.

*Hips.*—Color: Green Group 141B. Shape: Cupped. Size: 2 cm in diameter.

PLANT

*Form.*—Shrub.

*Growth.*—Vigorous and branching.

*Age at maturity.*—Two years.

*Mature plant.*—Height: 120 cm in England; two meters or greater in U.S. Width: 90 cm

*Rootstock.*—Dr. Huey in the United States. *Rosa dumetorum laxa* for the observed plants in the United Kingdom.

Foliage: Number of leaflets on normal mid-stem leaves: 7.

*Size.*—Medium. About 17.5 cm long×13 cm wide.

*Quantity.*—Normal.

*Color.*—New foliage: Upper side: Yellow-Green Group 146B. Lower side: Yellow-Green Group 146C. Old foliage: Upper side: Green Group 139A. Lower side: Yellow-Green Group 147B.

Leaflets:

*Size.*—About 7.2 cm long×4.7 cm wide.

*Shape.*—Broadly oval and pointed oval.

*Base shape.*—Cordate.

*Apex shape.*—Cuspidate.

*Texture.*—Leathery.

*Edge.*—Serrated.

*Serrations.*—Double and small.

*Petiole.*—Color: Greyed-Red Group 178B.

*Petiole rachis.*—Color: Yellow-Green Group 144B. Underside: Prickles.

*Auricle shape.*—Long point.

*Stipules.*—Length: 3 cm; smooth.

*Disease resistance.*—Resistant to mildew, blackspot and rust under normal growing conditions.

*Pest persistence.*—Not tested.

*Vein color.*—Yellow-Green Group 146B.

*Venation pattern.*—Branching.

Wood:

*New wood.*—Color: Greyed-Orange Group 176C. Bark: Smooth.

*Old wood.*—Color: Yellow-Green Group 144A. Bark: Rough.

Prickles:

*Quantity.*—On main canes from base: 62 per 70 cm length. On laterals from main canes: 8 per 40 cm length.

*Form.*—Hooked downward.

*Length.*—8 mm.

*Color when young.*—Greyed-Orange Group 175B.

*Color when mature.*—Greyed-Orange Group 176C.

Small prickles:

*Quantity.*—On main stalks: Many. On laterals: Many.

*Color.*—When young: Greyed-Red Group 178B. When mature: Greyed-Orange Group 175B.

Winter hardiness: Not tested.

I claim:

1. A new and distinct variety of rose plant of the shrub/climber class, substantially as herein shown and described, characterized particularly by its soft pink, cupped flowers filled with numerous petals; vigorous, bushy growth, and good fragrance with a hint of myrrh.

* * * * *

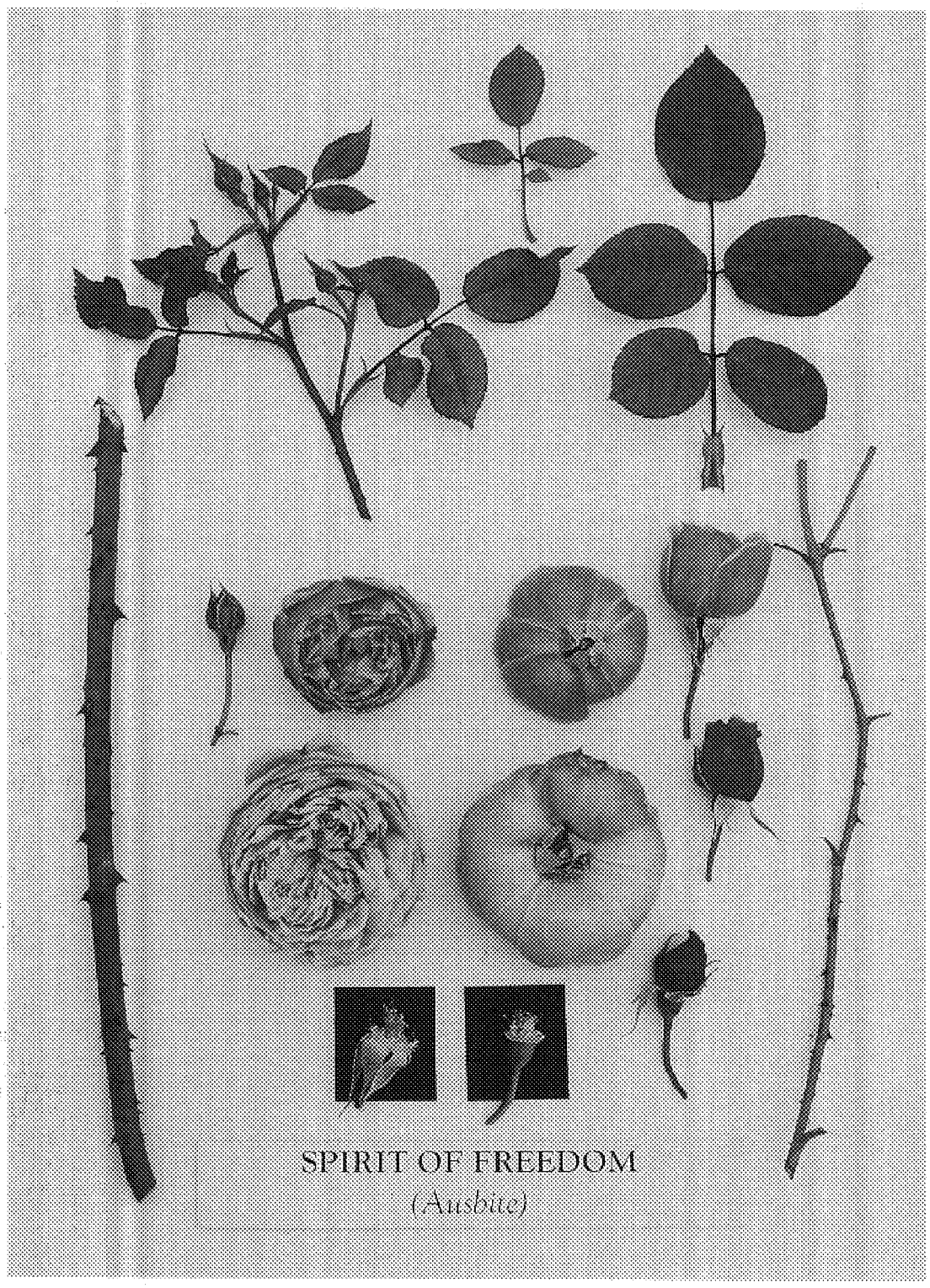
SPIRIT OF FREEDOM
(Ausbite)